United States Patent

Maeda et al.

Patent Number: 5,370,612
Date of Patent: Dec. 6, 1994

[54] INFUSION APPARATUS CAPABLE OF MEASURING A FLUID DELIVERY RATE TAKING A DEAD BAND INTO ACCOUNT

[75] Inventors: Akihiro Maeda, Souraku, Japan; Thomas Callaghan, Algonquin, Ill.

[73] Assignees: Sharp Kabushiki Kaisha, Osaka, Japan; Baxter International Incorporated, Deerfield, Ill.

[21] Appl. No.: 42,004

[22] Filed: Apr. 2, 1993

[30] Foreign Application Priority Data

Apr. 3, 1992 [JP] Japan .................. 4-81968

[51] Int. Cl.⁵ .............................. A61M 31/00
[52] U.S. Cl. ............................ 604/67; 604/65; 604/151; 604/154; 128/DIG. 12; 128/DIG. 13; 417/22; 417/63
[58] Field of Search ............. 128/DIG. 12, DIG. 13; 604/65, 67, 151, 152, 153, 154, 155; 417/63, 22

[56] References Cited

U.S. PATENT DOCUMENTS

| | | | |
|---|---|---|---|
| 4,067,332 | 1/1978 | O'Leary | 604/152 |
| 4,498,843 | 2/1985 | Schneider et al. | 604/65 |
| 4,501,531 | 2/1985 | Bilstad et al. | 604/67 |
| 4,559,044 | 12/1985 | Robinson et al. | 604/65 |
| 4,602,249 | 7/1986 | Abbott | 128/DIG. 12 |
| 4,636,144 | 1/1987 | Abe et al. | 604/153 |
| 4,731,057 | 3/1988 | Tanaka et al. | 604/153 |
| 4,846,637 | 7/1989 | Alderson et al. | 604/153 |
| 4,850,805 | 7/1989 | Madsen et al. | 604/153 |
| 4,919,650 | 4/1990 | Feingold et al. | 604/67 |
| 5,068,586 | 11/1991 | Kawahara et al. | |

FOREIGN PATENT DOCUMENTS

| | | | |
|---|---|---|---|
| 0319267 | 6/1989 | European Pat. Off. | 604/153 |
| 6443936 | 3/1989 | Japan. | |
| 177754 | 5/1989 | Japan. | |
| 332396 | 2/1991 | Japan. | |

*Primary Examiner*—C. Fred Rosenbaum
*Assistant Examiner*—N. Kent Gring

[57] ABSTRACT

A slit disk having a hole at a specified portion of its flat surface and a plurality of slits at regular intervals at a peripheral portion thereof is mounted to a shaft of an infusion pump. A controller clears a live band determination counter based on a light detection signal from a sensor when the hole is detected, and increments the count value of a live band determination counter when an side edge of one of the plurality of slit is detected. When the count value of the live band determination counter falls within "10" to "24" or "0" to "2", it is determined that the infusion pump is in a live band, and the count value of the live band counter is incremented. Thus an operation amount of the infusion pump in the live band is detected to measure a fluid delivery rate taking a dead band into account.

22 Claims, 7 Drawing Sheets

INFUSION APPARATUS CAPABLE OF MEASURING A FLUID DELIVERY RATE TAKING A DEAD BAND INTO ACCOUNT

BACKGROUND OF THE INVENTION

1. Field of the Invention

The present invention relates to an improved infusion apparatus.

2. Description of the Prior Art

FIG. 4 is a simplified block diagram of a conventional infusion apparatus and FIG. 5 is a sectional view of an infusion pump. Referring to FIG. 4, a conventional infusion apparatus has an infusion pump 2 driven by a motor 1 to administer medication to a patient. The infusion pump 2 is constructed as shown in FIG. 5, and includes a housing 11, bearings 12, a shaft 13, cams 14, fingers 15, and a pressure plate 16. The aforementioned infusion pump 2 delivers fluid such as a solution through an administration tube 17 in the following manner.

When the shaft 13 is driven to rotate by the motor 1 (refer to FIG. 4), a plurality of cams 14, 14, ... mounted around the shaft 13 rotate. Each cam 14 has a circular form and is secured eccentrically to the shaft 13 so that it has a maximum radius $a_1$ and a minimum radius $a_2$. In the present example, eight of the above-mentioned type cams 14 are mounted around the shaft 13.

Then, the cams 14 mounted around the shaft 13 are shifted in angle between adjacent ones by 45° (360°/8). Consequently, the cams 14 are arranged so that the cams 14 gradually change their radii each from the maximum radius $a_1$ to the minimum radius $a_2$ and then from the minimum radius $a_2$ to the maximum radius $a_1$ toward the pressure plate 16 in a phase shift manner. With the above-mentioned arrangement, the cams 14 ... rotate in company with the rotation of the shaft 13 to achieve a wave-like movement of the circumferences of the cams 14.

The cams 14 are rotatably inserted in the aforementioned fingers 15. When the shaft 13 rotates to rotate the cams 14, end portions 15a of the fingers 15 slide in a direction perpendicular to the shaft 13 synchronously with the movement in radial direction of the cams 14. Therefore, by arranging in a direction perpendicular to the pressure plate 16 the end portions 15a, of the eight fingers in which the eight cams 14 are inserted, the end portions 15a of the eight fingers 15, move in a wave-like manner in accordance with the rotation of the cams 14. In other words, the end portions 15a, of the eight fingers move in a peristaltic manner in company with the rotation of the shaft 13.

Between the end portions 15a of the fingers 15 and the pressure plate 16 is interposed the administration tube 17. When each of the end portions 15a of the eight fingers 15, 15, ... is put in a position closest to the administration tube 17, the end portion 15a of the finger 15 presses the administration tube 17. Then by rotating the shaft 13 to peristaltically move the end portions 15a of the fingers 15, 15, the end portions 15a of the fingers 15, consecutively occlude the administration tube 17 from an upper portion to a lower portion to push downward the medication fluid through the administration tube 17 to thereby transfer the medication fluid.

The infusion pump 2 having the above-mentioned construction is driven by the motor 1 under the control of a controller 3 as shown in FIG. 4.

FIG. 6 shows a detailed block diagram of the controller 3. The following describes the controller 3 with reference to FIG. 6.

A key panel 21 includes various operation keys such as numeral keys for inputting values of fluid infusion rate, volume to be infused (referred to as VTBI hereinafter), and the like for operating the infusion pump 2, control keys for input assistance, a start key for starting a fluid infusion, a stop key for stopping the fluid infusion, and a call-up key for displaying volume infused (referred to as VI hereinafter) and the like.

Data of the fluid infusion rate and VTBI input from the key panel 21 are displayed on a programming display section 22 for confirmation by a doctor or nurse.

After the various data are input in a manner as described above, fluid infusion is initiated by the start key. Then the aforementioned motor 1, which is a stepping motor, is driven by a motor driving circuit 23 to rotate the shaft 13 of the infusion pump 2 (refer to FIG. 4) and thereby peristaltically move the fingers 15 to effect fluid infusion.

A rotation amount of the infusion pump 2 is detected by a pump rotation detector 4 described in detail hereinafter, and a CPU (Central Processing Unit) 24 detects the fluid infusion rate according to a detection result from the pump rotation detector 4.

During the fluid infusion operation, a variety of safety devices described as follows are used to safely operate the infusion apparatus.

First, an upstream occlusion sensor 25 detects a pressure-reduction state within the administration tube 17 due to the occurrence of occlusion (e.g., clogged filter) between a medical solution container (not shown) containing a medication fluid and the infusion pump 2, and outputs a digital signal representing the occlusion/non-occlusion state.

A downstream occlusion sensor 26 detects a pressure-rise condition within the administration tube 17 due to the occurrence of occlusion between the infusion pump 2 and the patient, and outputs a digital signal representing the occlusion/non-occlusion state.

An air bubble detector 27 detects an air bubble inside the administration tube 17, and outputs an analog signal representing the size of the air bubble.

A door opening detector 28 detects that a door of the infusion apparatus is open, and outputs a digital signal representing the open/closed state of the door. The inner surface of the door of the infusion apparatus concurrently serves as the pressure plate 16. Inside the door is provided the upstream occlusion sensor 25, the downstream occlusion sensor 26, the air bubble detector 27, and the like. The infusion apparatus does not function when the door is open, and therefore the fact that the door is open must be securely detected when the infusion apparatus is in operation.

A battery voltage detector 29 detects the voltage level of a battery and outputs an analog signal representing the voltage level.

An analog-to-digital (A/D) converter 30 takes in an analog signal representing the motor current level from the motor driving circuit 23, the analog signal representing the size of the air bubble from the air bubble detector 27, and the analog signal representing the voltage level from the battery voltage detector 29, and converts the analog signals into digital signals to output the resulting digital signals to the CPU 24.

Thus the CPU 24 can detect the existence of an air bubble having a size greater than a prescribed value and an abnormal drop of the battery voltage based on the digital signals from the A/D converter 30. Furthermore, the CPU 24 detects the occlusion of a fluid transfer system and a door open state based on the digital signals from the upstream occlusion sensor 25, the downstream occlusion sensor 26, and the door opening detector 28.

An alarm/alert display section 31 is driven by the CPU 24 to display alarm or alert messages of the upstream occlusion condition, downstream occlusion condition, the existence of an air bubble greater than a prescribed size, an open condition of the door, and an abnormal drop of the battery voltage.

Furthermore, a buzzer 33 is driven by a alarm/alert buzzer driving circuit 32 to inform the doctor or nurse of the alarm/alert by means of the buzzer sound.

A panel lock switch 34 serves to render the keys of the key panel 21 and the power key input-inhibited so that the infusion apparatus will not be operated by any person other than doctors or nurses.

An operation indicator lamp 35 indicates that the apparatus is currently in a state of fluid infusion operation, alarm, or alert.

A RAM (Random Access Memory) 7 stores a variety of data to be used for operation of the CPU 24. In the RAM 7, a counter whose initial value is the VTBI input from the key panel 21 and an edge counter for counting a rotation amount of the infusion pump 2 as described hereinafter and VI are set up.

A ROM (Read Only Memory) 36 stores a program for operating the controller 3.

In order to inform the doctor or nurse of the VTBI or volume to be infused (i.e., the current scheduled fluid volume) and the VI or total volume infused (i.e., the current cumulation volume) while administering medication fluid to a patient by means of the infusion apparatus, it is necessary to measure the current fluid delivery rate of the infusion pump 2.

Conventionally, the measurement of the fluid delivery rate of the infusion pump 2 has been performed by means of the aforementioned pump rotation detector 4, the controller 3, and the RAM 7 in the following manner.

Referring to FIG. 4, the pump rotation detector 4 mainly includes a slit disk 6 mounted to the shaft 13 at an end opposite to the motor 1 of the infusion pump 2 and a sensor 5 which is mounted so that it extends over both surfaces of a peripheral portion of the slit disk 6. At the peripheral portions of the slit disk 6 are formed a plurality of slits (not shown) extending radially at regular intervals to the circumferential direction. The sensor 5 detects light which has passed through the slit portion of the slit disk 6 rotating, and outputs a light detection signal.

The light detection signal output from the sensor 5 in a manner as described above is transmitted to the controller 3.

Then the controller 3 detects the amount of change from the slit portion to the non-slit portion or from the non-slit portion to the slit portion (referred to as the "rotation amount" hereinafter) of the rotating slit disk 6 based on the light detection signal. Based on the detected rotation amount, the fluid infusion rate, i.e. the fluid delivery rate is detected.

FIG. 7 shows a flowchart of the fluid infusion rate detection operation executed by the controller 3. The following describes the fluid infusion rate detection operation with reference to FIG. 7.

It is noted that an incremental unit (i.e., the amount of fluid flow made in one operation cycle of the infusion pump 2) is assumed to be 0.1 ml in the present apparatus.

When the aforementioned motor 1 is rotating, the count value of an edge counter is incremented every time each of two side edges of a sector passes through the sensor 5 based on the light detection signal from the sensor 5 (step S1 through step S3).

When the resulting edge count value reaches a preset edge count value corresponding to the incremental unit of 0.1 ml (i.e., a value two times as many as the slit amount provided in the slit disk 6), the count value of a VTBI (i.e., volume to be infused) counter set in the RAM 7 is decreased by the incremental unit while the count value of a VI (i.e., volume infused) counter is increased by the incremental unit. Thereafter, the count value of the edge counter is cleared (step S4 and step S5).

When the count value of the VTBI counter counted down is not "0", the program flow returns to step S1 to enter into a process of measuring the next unit flow. Otherwise, the fluid delivery rate detection operation ends (step S6).

Then the incremented count values of the VTBI counter and the VI counter are read out from the RAM 7 as needed, and the VTBI and the VI are displayed on a display unit 8.

Because the fingers 15 move peristaltically downward in the infusion pump 2, there is an intermission in medication fluid delivery after the lowermost finger 15 has finished pressing the administration tube 17 until the second uppermost finger 15 begins to press the administration tube 17.

The above-mentioned intermission in medication fluid delivery is referred to as the "dead band" and the period for which the medication fluid is flowing is referred to as the "live band" hereinafter.

The aforementioned conventional measurement of the fluid delivery rate has been performed by continuously detecting the rotation amount of the rotating slit disk 6 by means of the aforementioned controller 3 to detect the incremental unit, and therefore the incremental unit has been detected on the assumption that fluid delivery is effected even in the dead band.

Consequently, there has been a problem that the VTBI and the VI displayed on the display unit 8 differ from the actual values.

When the fluid delivery rate to be detected is not smaller than the fluid flow in one operation cycle of the infusion pump 2 (incremental unit), the fluid delivery rate can be detected with certain accuracy by taking into account the loss in fluid delivery due to the dead band in one operation cycle of the shaft 13 of the infusion pump 2. However, when the fluid delivery rate to be detected is smaller than the above-mentioned unit flow, there is no way for perceiving how much edges related to the dead band exist in the detected edges. Therefore, it is impossible to detect any fluid delivery rate smaller than the unit flow.

SUMMARY OF THE INVENTION

The object of the present invention is therefore to provide an infusion apparatus capable of correctly measuring a fluid delivery rate even smaller than the unit flow taking the dead band into account.

In order to achieve the aforementioned object, there is provided an infusion apparatus having an infusion pump which includes a live band when a fluid transfer is effected and a dead band when no fluid transfer is effected in one operation cycle of the infusion pump and operates to transfer a fluid through an administration tube, the infusion apparatus comprising: a plurality of mark means provided at every specified angle of rotation in a specified portion of a rotary member rotating together with the infusion pump, said specified portion corresponding to the live band of the infusion pump; mark detection means for detecting the mark means to output a mark detection signal; and pump operation amount detection means for detecting the operation amount of the infusion pump in the live band by counting the amount of the mark means detected by the mark detection means based on the mark detection signal output from the mark detection means, a fluid delivery rate of the infusion pump being determined based on the operation amount of the infusion pump in the live band detected by the pump operation amount detection means.

According to the infusion apparatus of the present invention, the infusion pump is rotated to transfer the fluid through the administration tube. Then, the mark means provided at the portion corresponding to the live band in the rotary member is detected by the mark detection means, and a mark detection signal is output from the mark detection means.

Then the amount of the detected mark means is counted by the pump operation amount detection means based on the mark detection signal output from the mark detection means. In the above case, the mark means is provided at every specified angle of rotation, and therefore the pump operation amount detection means can detect the rotation amount i.e. the operation amount of the infusion pump in the live band by the amount of the mark means counted.

Therefore, by setting up the fluid flow in one operation cycle of the infusion pump at a specified value, the fluid delivery rate is detected based on the operation amount of the infusion pump.

It is preferable that said rotary member is a disk mounted on a rotary shaft of the infusion pump, the mark means is edges of slits provided radially at a peripheral portion of the disk, and the mark detection means is a photosensor.

With the above arrangement, when the passage of an edge of the slit provided radially at a peripheral portion corresponding to the live band of the disk mounted to the rotary shaft of the infusion pump is detected by means of a photosensor, the aforementioned mark detection signal is output from the photosensor.

Thus by detecting the edge of the slit of the disk mounted to the rotary shaft of the infusion pump by means of the photosensor, the fluid delivery rate is simply detected.

Also, there is provided an infusion apparatus having an infusion pump which includes a live band when a fluid transfer is effected and a dead band when no fluid transfer is effected in one operation cycle of the infusion pump and operates to transfer a fluid through an administration tube, the infusion apparatus comprising: reference mark means provided at a rotary member rotating with the infusion pump, said reference mark means representing a reference position of the rotary member; a plurality of mark means provided at every specified angle of rotation at the rotary member; mark detection means for detecting the reference mark means and the mark means to output a reference mark detection signal and a mark detection signal; counter means of which a count value is cleared based on the reference mark detection signal and incremented based on the mark detection signal; live band determination means for determining that the infusion pump is in the live band according to a specified procedure based on the count value of the counter means; and pump operation amount detection means for detecting the operation amount of the infusion pump by counting the amount of the mark means detected in the live band based on the mark detection signal output from the mark detection means in a band when it is determined that the infusion pump is in the live band by the live band determination means, a fluid delivery rate of the infusion pump being determined based on the operation amount of the infusion pump in the live band detected by the pump operation amount detection means.

According to the infusion apparatus, the infusion pump is rotated to transfer the fluid through the administration tube. In the above case, the reference mark means and the mark means provided in the rotary member are detected by the mark detection means to output the reference mark detection signal and the mark detection signal from the mark detection means.

Then the count value of the counter means is cleared based on the reference mark detection signal, while the count value of the counter means is incremented based on the mark detection signal.

Then it is determined in a predetermined manner whether or not the infusion pump is in the live band and actually transferring fluid by the live band determination means based on the incremented count value of the counter means.

Consequently, when it is determined that the infusion pump is in the live band, the amount of the mark means detected in the live band is counted by the pump operation amount detection means based on the mark detection signal output from the mark detection means. In the above case, the mark means is provided at every specified angle of rotation at the rotary member, and therefore the pump operation amount detection means can detect the operation amount of the infusion pump in the live band according to the amount of the mark means counted.

Therefore, by setting up the fluid flow in one operation cycle of the infusion pump at a specified value, the fluid delivery rate is detected based on the operation amount of the infusion pump.

It is preferable that said rotary member is a disk mounted on a rotary shaft of the infusion pump, the reference mark means is a mark provided on a flat surface of the disk, the mark means is edges of slits provided radially at a peripheral portion of the disk, and the mark detection means is a photosensor.

With the above arrangement, when a mark provided on the flat surface of the disk mounted to the rotary shaft of the infusion pump is detected by the photosensor, the photosensor outputs the reference mark detection signal. Furthermore, when the passage of an edge of the slit provided radially at a peripheral portion of the disk is detected by the photosensor, the photosensor outputs the mark detection signal.

Thus by detecting the mark and the slit edge provided at the disk mounted to the rotary shaft of the infusion pump by means of the photosensor, the fluid delivery rate is simply detected.

It is preferred that the live band determination means determines that the infusion pump is in the live band when the count value of the counter means is in a count value range corresponding to the case where the infusion pump is in the live band.

With the above arrangement, the count value of the counter means is taken in by the live band determination means. When the count value taken in falls within the count value range corresponding to the case where the infusion pump is in the live band, it is determined that the infusion pump is in the live band. Thus the live band is simply and surely determined.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

The following describes in detail the present invention with reference to embodiments shown in the attached drawings.

Figure 1:
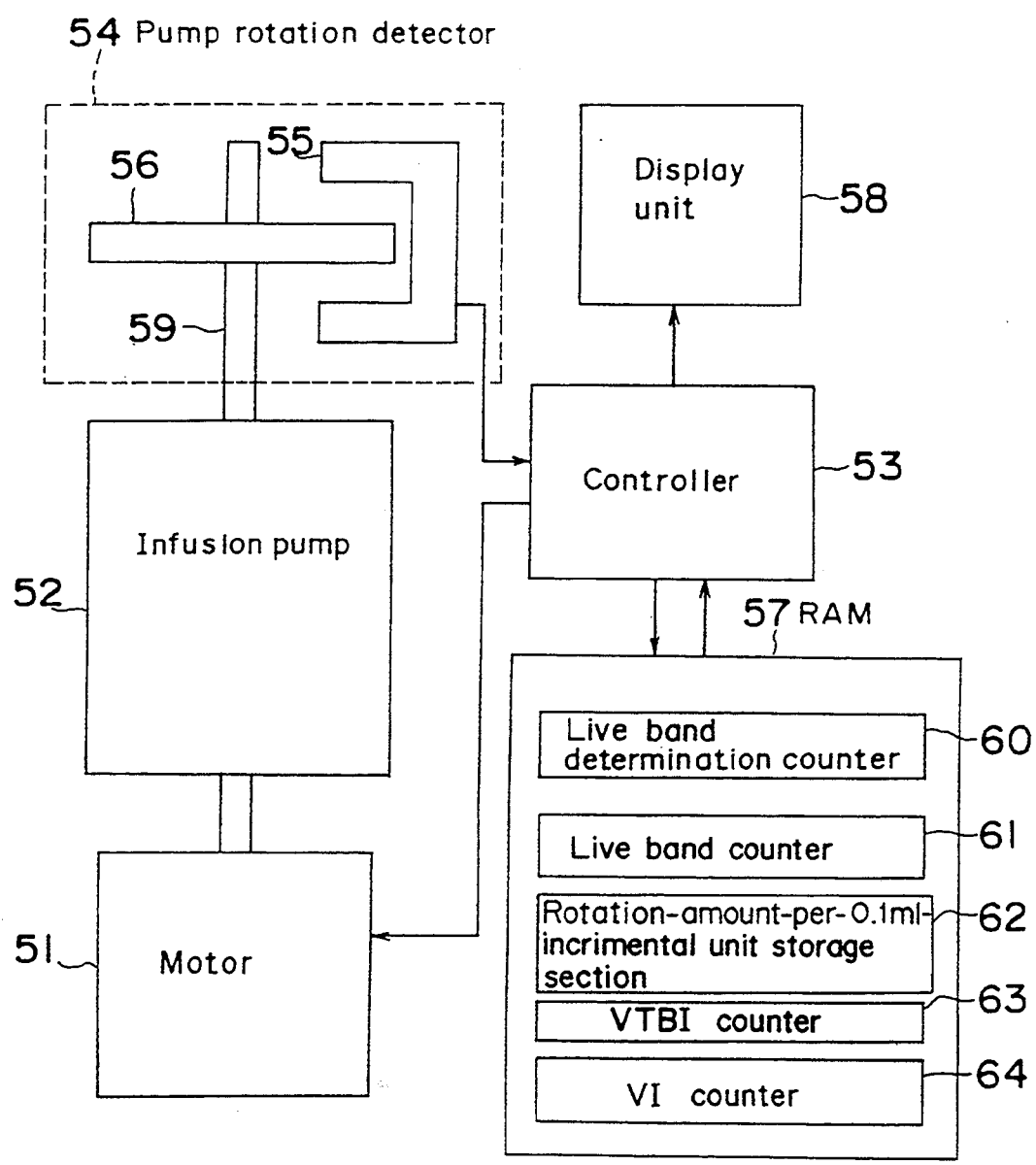
FIG. 1 is a simplified block diagram of an infusion apparatus in accordance with the present invention.
Figure 4:
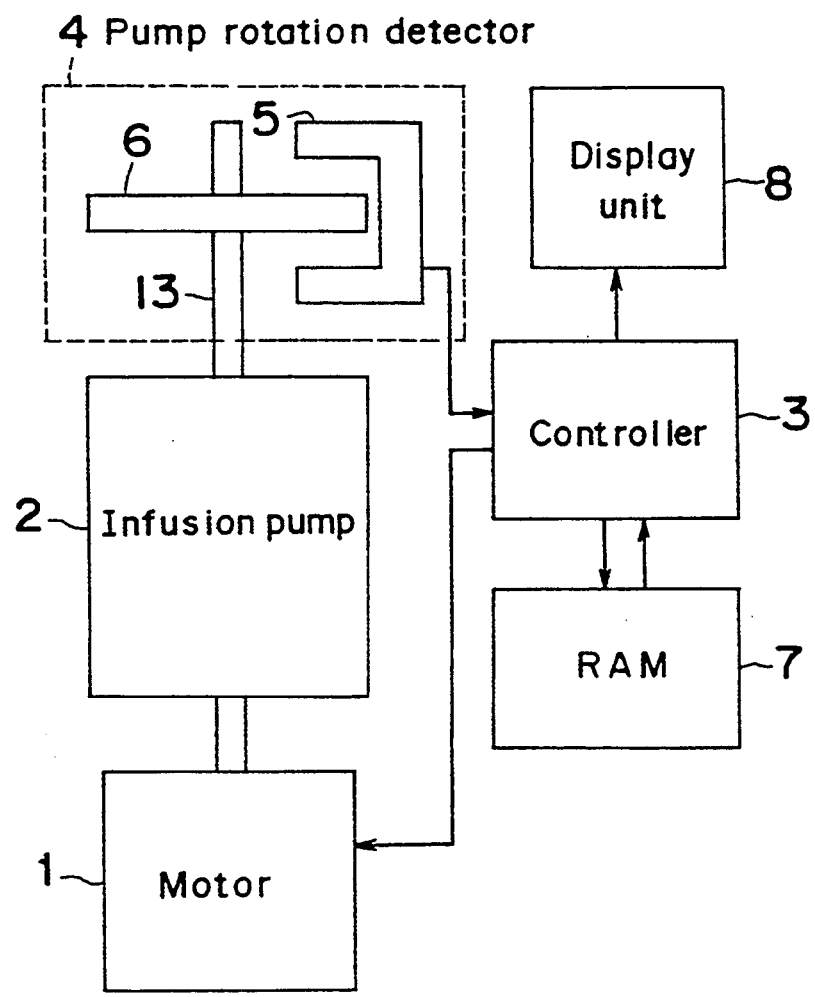
FIG. 4 is a simplified block diagram of a conventional infusion apparatus.
Figure 5:
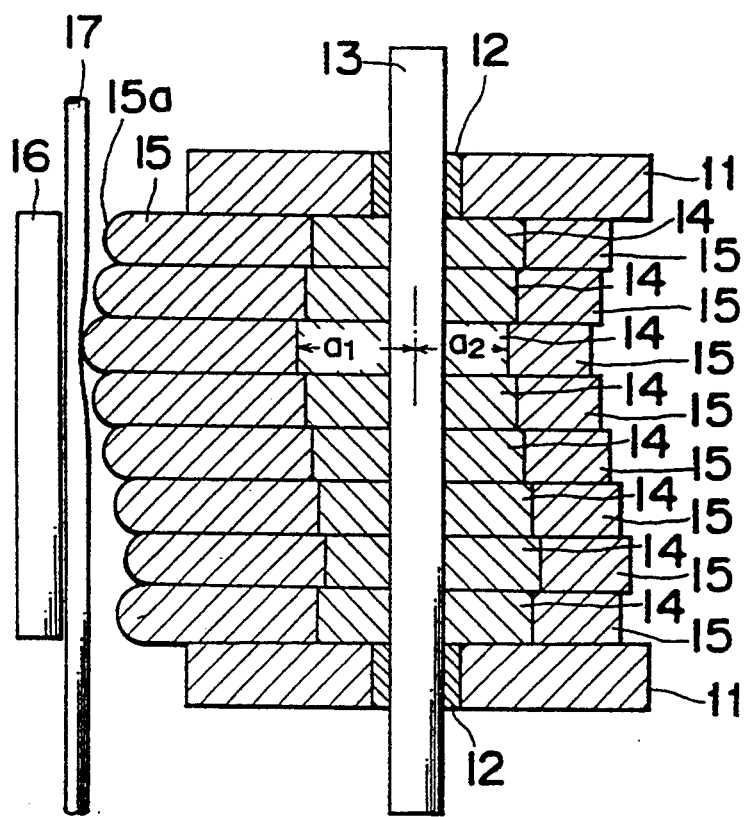
FIG. 5 is a section view of the infusion pump shown in FIG. 4.

FIG. 1 is a simplified block diagram of an infusion apparatus for administering medication in accordance with the present invention. A motor 51 and an infusion pump 52 in the infusion apparatus is the same as the motor 1 and the infusion pump 2 in the conventional infusion apparatus shown in FIG. 4.

In a RAM 57, there are set up a live band determination counter 60, a live band counter 61, a VTBI counter 63, and a VI counter 64, and a rotation amount corresponding to an incremental unit of 0.1 ml is stored in a rotation-amount-per-0.1 ml-unit-flow storage section 62.

The initial value of the VTBI counter 63 is to be preset by numeral keys on a key panel of a controller 53.

Figure 2:
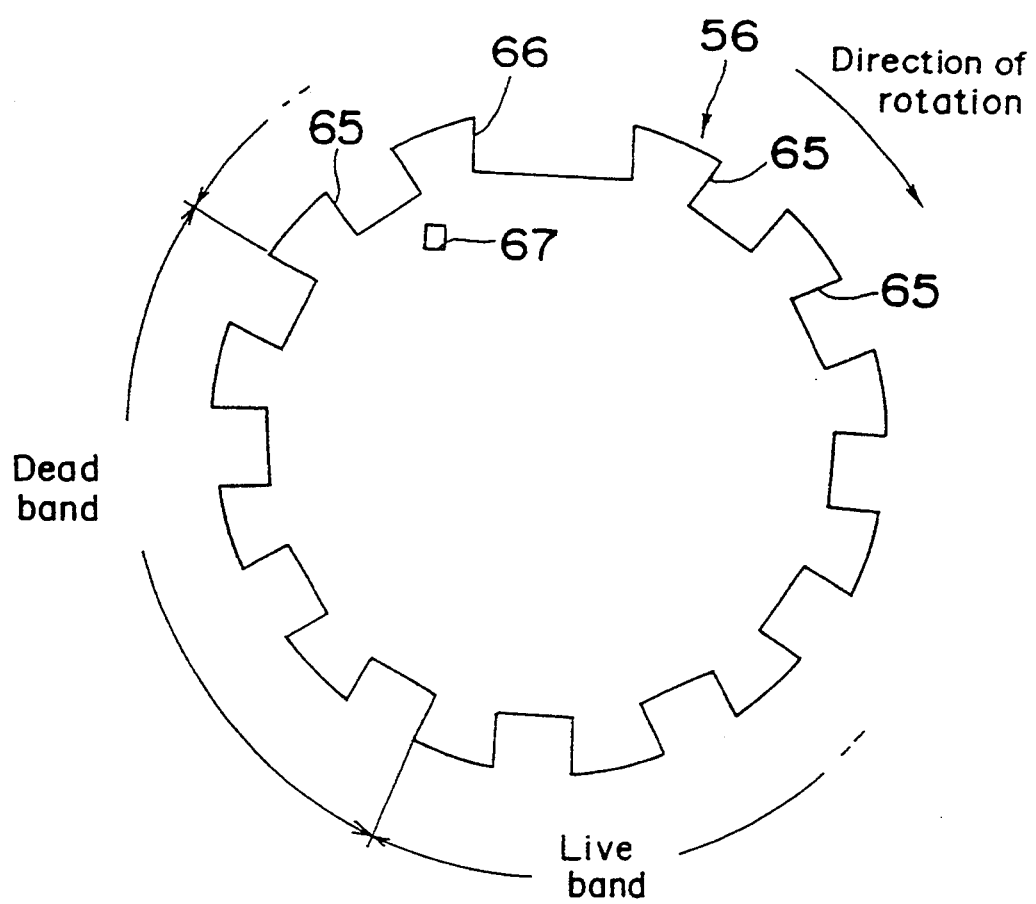
FIG. 2 is a plan view of an example of a slit disk shown in FIG. 1.

FIG. 2 shows a plan view of a slit disk 56 mounted on a shaft 59 of the infusion pump 52 in the present embodiment. At a peripheral portion of the slit disk 56 are provided twelve slits 65 at regular intervals. It is noted that a slit (reference slit) 66 provided at a reference position of the slit disk 56 is made to have a width greater than the width of the other slits 65 to allow an easy detection of the reference position.

Furthermore, a hole 67 is provided at a root portion of the slit 65 located behind the reference slit 66 in the direction of rotation of the slit disk 56.

The dead band of the slit disk 56 is so arranged as to cover four slits 65 as indicated by an arrow in FIG. 2.

A sensor 55 shown in FIG. 1 detects light which has passed through the slits 65 and 66 as well as the hole 67 of the rotating slit disk 56 and transmits the resulting light detection signal to a controller 53. Then the controller 53 counts the amount of edges of sectors, i.e. the amount of rotation based on the light detection signal from the sensor 55. Based on the rotation amount, the fluid delivery rate is detected.

Figure 6:
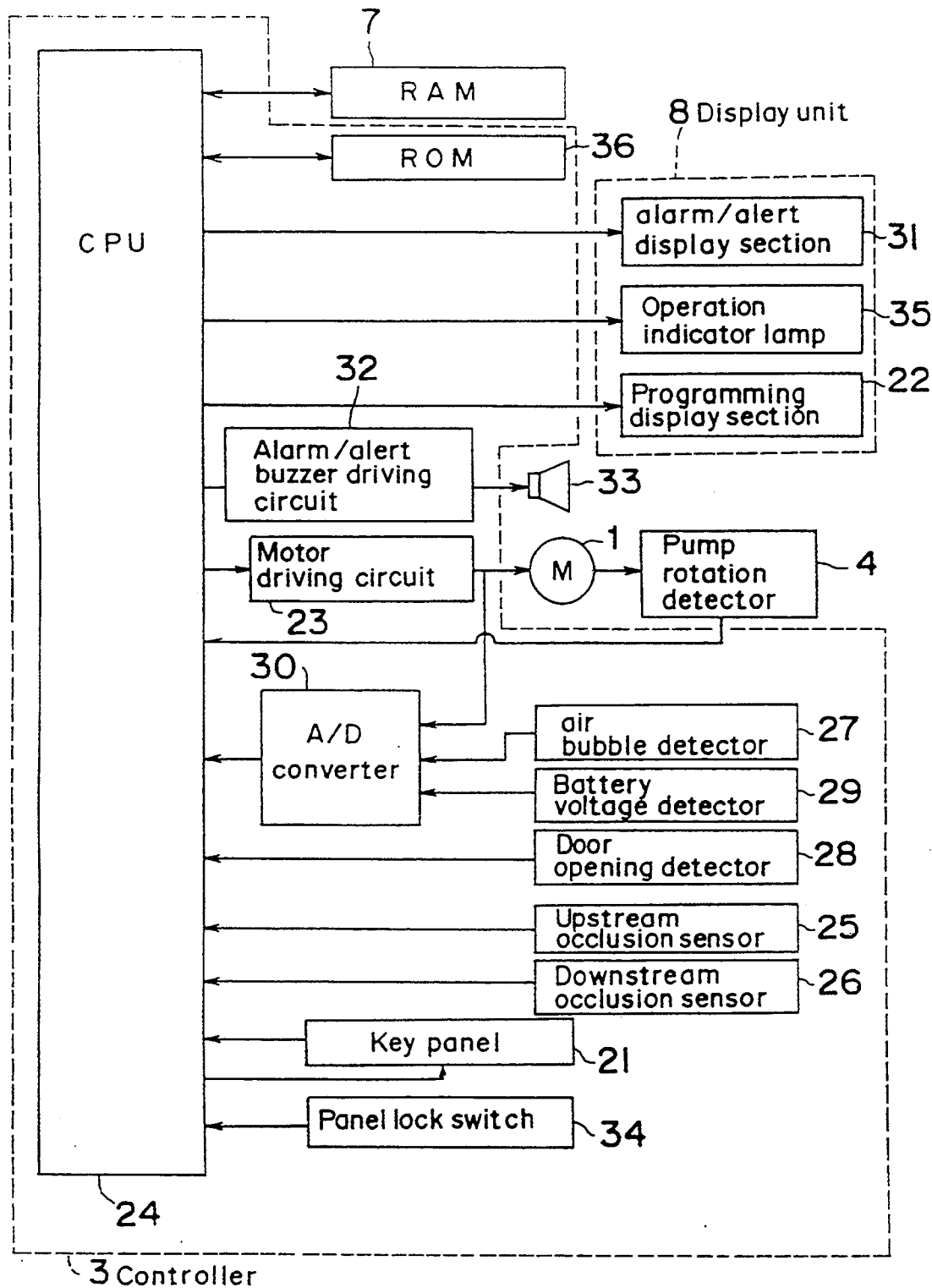
FIG. 6 is a detailed block diagram of the controller shown in FIG. 4.
Figure 7:
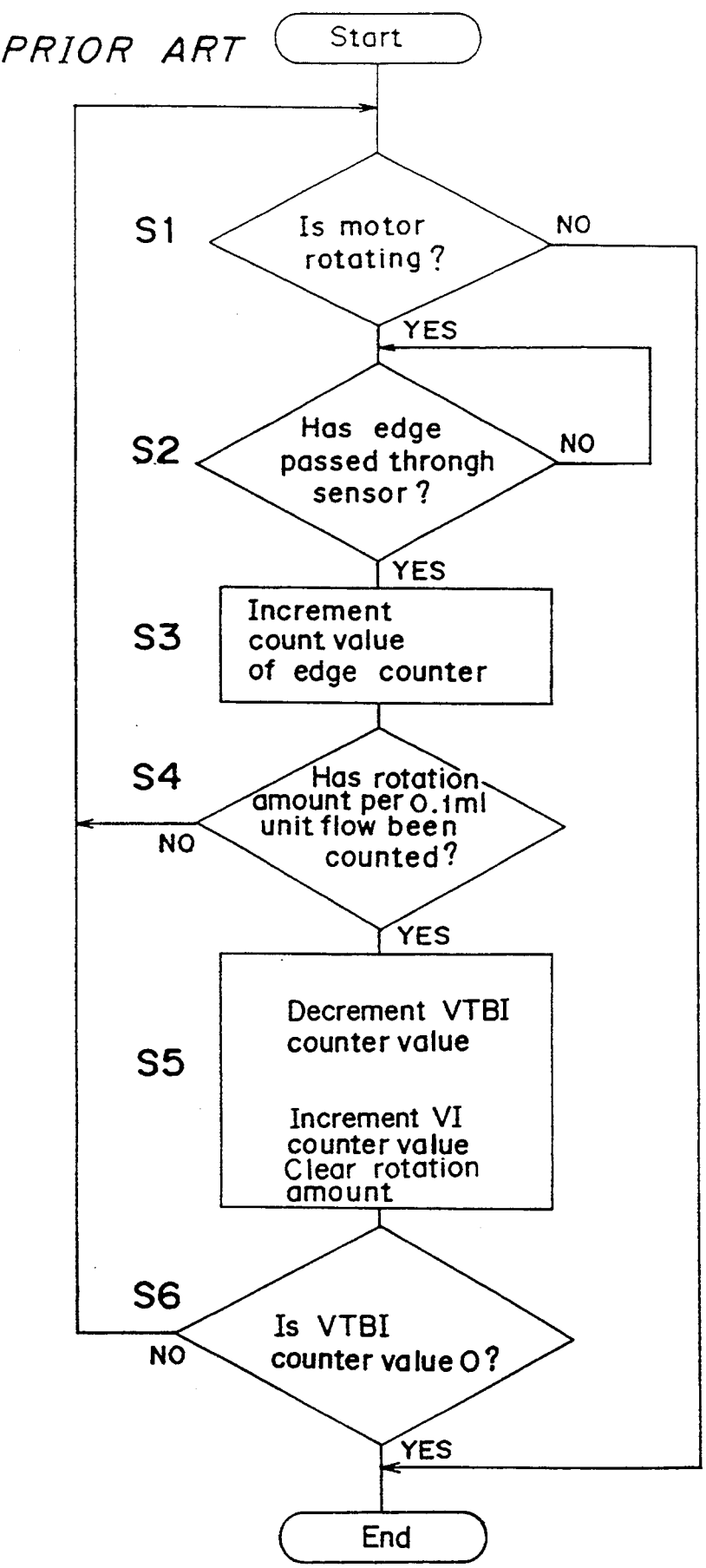
FIG. 7 is a flowchart of a fluid delivery rate detection operation of the conventional infusion apparatus shown in FIG. 4.

The controller 53 has the same fundamental structure as that of the controller 3 of the conventional infusion apparatus shown in FIG. 6.

Figure 3:
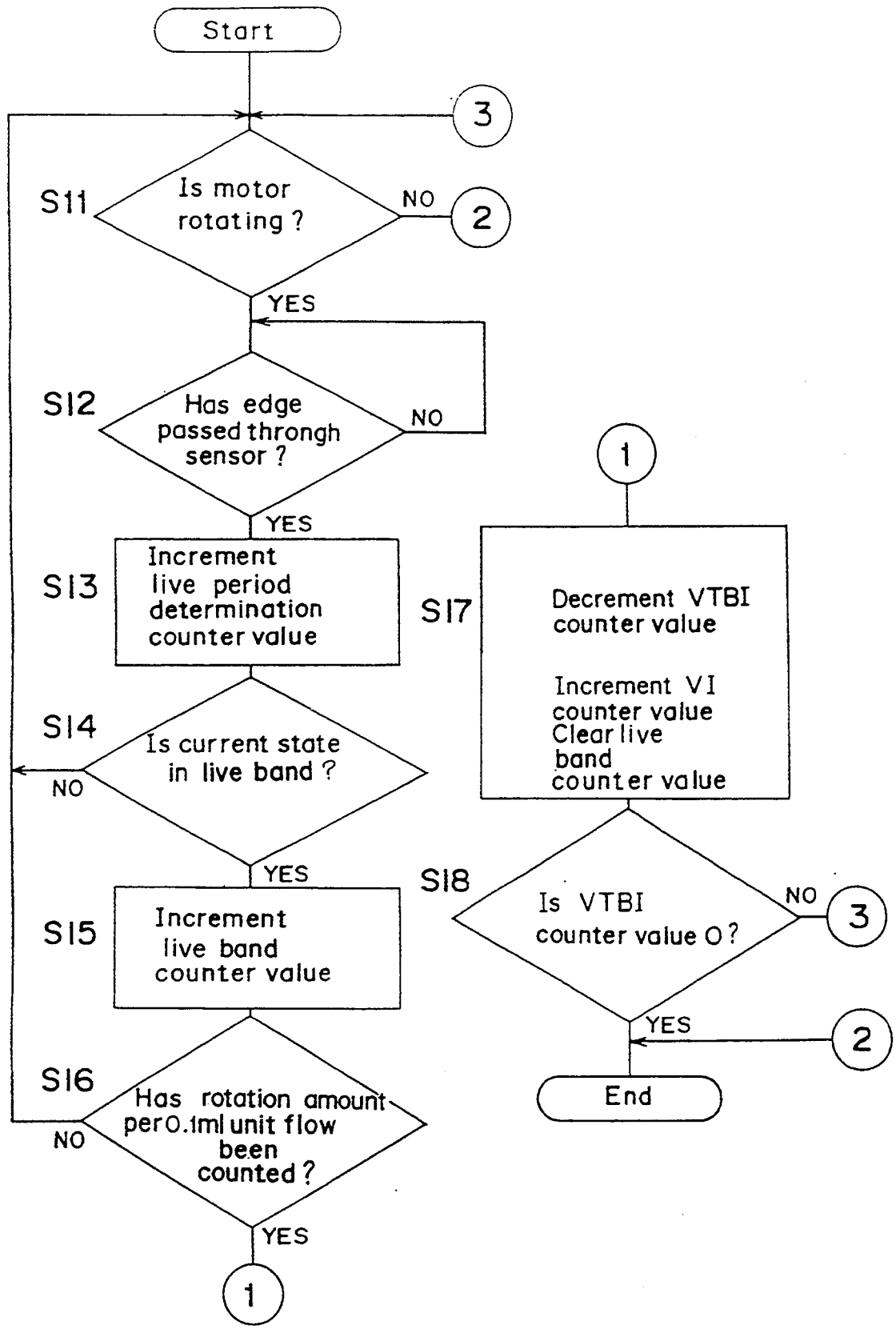
FIG. 3 is a flowchart of an exemplified fluid delivery rate detection operation executed by the controller shown in FIG. 1.

FIG. 3 shows a flowchart of the fluid delivery rate detection operation executed by the controller 53. The following describes in detail the fluid delivery rate detection operation with reference to FIG. 3. It is noted that the preferred incremental unit is 0.1 ml in the present embodiment.

It is determined whether or not the motor 51 is rotating at step S11. When the motor 51 is rotating, the program flow proceeds to step S12. If not, the fluid delivery rate detection operation ends.

It is then determined at step S12 whether or not an edge of a sector has passed through the sensor 55. When the edge has passed through the sensor 55, the program flow proceeds to step S13. If not, the program waits for the passage of the edge.

It is noted that the passage of the edge is determined according to the presence or existence of an illuminance change from bright to dark or from dark to bright in the light detection signal from the sensor 55.

The live band determination counter 60 is incremented at step S13.

The count value of the live band determination counter 60 is cleared when the hole 67 provided at the slit disk 56 is detected by the sensor 55. Therefore, the live band determination counter 60 counts the rotation amount after the hole 67 has passed through the sensor 55.

In other words, the hole 67 constitutes a reference mark means, the edges of the slits 65 and 66 constitutes a mark means, the sensor 55 constitutes a mark detection means, and the live band determination counter 60 and the controller 53 constitutes a counter means.

Therefore, if the relative positions of the hole 67 and the live band at the slit disk 56 are previously known, it can be determined whether or not the current state is in the live band or in the dead band by means of the rotation amount after detecting the hole 67.

In the present embodiment, the pump enters into the dead band at the second edge after detecting the hole 67, and then exits the dead band at the ninth edge of slits 65 to enter into the live band.

It is determined at step S14 whether or not the current state is in the live band based on the count value of the live band determination counter 60 after the increment at step S13. When the current state is in the live band, the program flow proceeds to step S15. If it is not, the program flow returns to step S11 to count the next rotation amount.

Whether or not the current state is in the live band is determined in the following manner. When the slit disk 56 of the present embodiment is used as described above, the band from the detection of the second side edge to the detection of the ninth side edge of slits 65 after detecting the hole 67 is the dead band. Therefore, when the count value of the live band determination counter 60 is "10" to "24" or "0" to "2", it is determined that the current state is in the live band.

In order to measure the rotation amount in the live band, the count value of the live band counter 61 is incremented at step S15.

Then it is determined at step S16 whether or not the rotation amount corresponding to the unit flow of 0.1 ml has been counted based on the count value of the live band counter 61 incremented at step S15. When the rotation amount corresponding to the unit flow of 0.1 ml has been counted, the program flow proceeds to step S17. If not, the program flow returns to step S11 to count the next rotation amount.

Whether or not the rotation amount corresponding to the preferred incremental unit of 0.1 ml has been counted is determined by comparing the count value of the live band counter 61 and the rotation amount stored in the rotation-amount-per-0.1 ml-incremental-unit-storage section 62 of the RAM 57.

Since a fluid delivery rate of 0.1 ml, or the incremental unit has been made, the count value of the VTBI counter 63 is decreased by a number corresponding to the incremental unit of 0.1 ml at step S17. Meanwhile, the count value of the VI counter 64 is increased by a number corresponding to the incremental unit of 0.1 ml.

Thus the operation concerning the unit flow detection has been completed, and then the count value of the live band counter 61 is cleared to be ready for the subsequent unit flow detection operation.

At the above time, the renewed count value of the VTBI counter 63 and the count value of the VI counter 64 are read out from the RAM 57, and the volume to be infused and the volume infused are displayed on a display unit 58.

Then it is determined at step S18 whether or not the renewed count value of the VTBI counter 63 is "0". Consequently, when the count value is not "0", the program flow returns to step S11 to continue the fluid delivery rate detection operation. When the count value is "0", it is determined that the delivery of the volume to be infused has been completed, and the fluid delivery rate detection operation ends.

According to the present embodiment as described above, the hole 67 is additionally provided at a specified position of the slit disk 56 for detecting the rotation of the infusion pump 52. It is also predetermined that the dead band ranges from the second side edge to the ninth side edge behind the position of the hole 67 of the slit disk 56.

In the RAM 57, there is set up the live band determination counter 60 of which count value is compulsorily cleared when the sensor 55 detects the hole 67 of the slit disk 56 and incremented when the sensor 55 detects each edge.

The aforementioned controller 53 determines that the current state is in the live band when the count value of the live band determination counter 60 is "10" to "24" or "0" to "2", and counts the rotation amount, i.e. the amount of edges in the band to detect the incremental unit (0.1 ml).

According to the present embodiment as described above, the fluid delivery rate can be detected based only on the rotation amount of the infusion pump 52 in the live band to allow a fluid delivery rate measurement taking the dead band into account.

Therefore, the fluid delivery rate can be measured correctly, and even a fluid delivery rate smaller than the incremental unit can be measured.

In the above embodiment, a pump rotation detector 54 is composed of the slit disk 56 and the sensor 55. However, the scope of the present invention is not limited to the above-mentioned construction. A key is that the apparatus includes reference mark means representing the reference position and mark means provided at every specified angle of rotation in the rotary member of the infusion pump as well as mark detection means for detecting the reference mark means and the mark means.

Although the infusion pump 2 has the construction in which the fluid transfer is achieved by the peristaltic movement of the fingers, the infusion pump of the present invention is not limited to that construction.

The fluid delivery rate detection operation process of the present invention is not limited to the flowchart shown in FIG. 3 of the above-mentioned embodiment.

The form of the slit of the slit disk of the infusion apparatus of the present invention is of course not limited to the form of the slit shown in FIG. 2.

At the peripheral portion of the slit disk 56 of the above-mentioned embodiment are provided the slits 55 and 56 throughout the entire circumference of the slit disk 56. The above arrangement is to make the slits 65 and 66 concurrently serve as slip detection slits for the motor 51. However, practically the slits 65 provided at the peripheral portion corresponding to the dead band are not necessary for the purpose of detecting the fluid delivery rate only in the live band.

Therefore, when the slip detection of the motor 51 is performed by another means, a fluid delivery rate detection operation taking the dead band into account can be performed by providing slits only at a peripheral portion corresponding to the live band at the slit disk.

In the above case, neither the hole 67 for determining the live band nor the live band determination counter 60 are necessary by providing slits at a peripheral portion corresponding to the live band.

Then by detecting each side edge of sector through the light detection signal from the sensor 55 to increment the count value of the live band counter 61, the live band counter 61 counts a rotation amount only in the live band as a matter of course.

As apparent in the above description, the infusion apparatus of an embodiment of the present invention is so constructed that the mark means provided at every specified angle of rotation at a potion corresponding to the live band in the rotary member rotating together with the infusion pump is detected by the mark detection means, and the amount of the detected mark means is counted by the pump operation amount detection means based on the mark detection signal from the mark detection means to detect the operation amount of the pump and thereby allow a fluid delivery rate measurement in the live band.

Therefore, according to the embodiment, even a fluid delivery rate smaller than the incremental unit can be correctly measured taking the dead band into account.

When the aforementioned rotary member is a disk mounted on a rotary shaft of the infusion pump, the aforementioned mark means is edges of slit provided radially at a peripheral portion of the disk, and the aforementioned mark detection means is the photosensor, a fluid delivery rate measurement is executed in a simple manner taking the dead band into account.

The infusion apparatus of another embodiment of the present invention is so constructed that a counter means of which count value is cleared based on a reference mark detection signal from mark detection means for detecting reference mark means and mark means provided at a rotary member rotating together with of the infusion pump and incremented by the mark detection signal is provided, the live band is determined by the live band discrimination means in a predetermined procedure based on the count value of the counter means, and the amount of the mark means detected in the live band is counted by the pump operation amount detection means to detect the pump operation amount to thereby allow a fluid delivery rate measurement only in the live band.

Therefore, according to the present embodiment, even a fluid delivery rate smaller than the unit flow can be correctly measured taking the dead band into account.

Another embodiment of the present invention is so constructed that the aforementioned live band determination means determines that the infusion pump is in the live band when the count value of the counter means is in the count value range corresponding to the case where the infusion pump is in the live band. Therefore, a secure discrimination between the live band and the dead band in one operation cycle of the infusion pump is achieved to allow a fluid delivery rate measurement taking the dead band into account to be executed.

The invention being thus described, it will be clear to one skilled in the art that the same may be varied in many ways. Such variations are not to be regarded as a departure from the spirit and scope of the invention, and all such modifications as would be clear to one skilled in the art are intended to be included within the scope of the following claims.

What is claimed is:

1. An infusion apparatus including an infusion pump having a live band when a fluid transfer is effected and a dead band when no fluid transfer is effected in one operation cycle of said infusion pump and operating operating to transfer a fluid through an administration tube, said infusion apparatus comprising:
   a plurality of mark means provided at every specified angle of rotation in a specified portion of a rotary member rotating together with the infusion pump, said specified portion corresponding to the live band of the infusion pump;
   mark detection means for detecting one of said plurality of mark means to output a mark detection signal; and
   pump operation amount detection means for detecting an operation amount of said infusion pump in the live band by counting a number of said plurality of mark means detected by said mark detection means based on the mark detection signal output from said mark detection means,
   wherein a fluid delivery rate of said infusion pump is determined based on the operation amount of said infusion pump in the live band detected by said pump operation amount detection means.

2. The infusion apparatus of claim 1, wherein said rotary member is a disk mounted on a rotary shaft of said infusion pump,
   said plurality of mark means are each an edge of a slit provided radially at a peripheral portion of the disk, and
   said mark detection means is a photosensor.

3. An infusion apparatus including an infusion pump having a live band when a fluid transfer is effected and a dead band when no fluid transfer is effected in one operation cycle of said infusion pump and operating to transfer a fluid through an administration tube, said infusion apparatus comprising:
   reference mark means provided on a rotary member rotating with said infusion pump, said reference mark means representing a reference position of said rotary member;
   a plurality of mark means provided at specified angles of rotation on said rotary member;
   mark detection means for detecting said reference mark means and one of said plurality of mark means to output a reference mark detection signal and a mark detection signal;
   counter means, whose count value is cleared based on the reference mark detection signal and incremented based on the mark detection signal;
   live band determination means for determining that said infusion pump is in the live band based on the count value of said counter means; and
   pump operation amount detection means for detecting an operation amount of said infusion pump by counting said plurality of mark means detected in the live band based on the mark detection signal output from said mark detection means in the live band,
   wherein a fluid delivery rate of said infusion pump is determined based on the operation amount of said infusion pump in the live band detected by said pump operation amount detection means.

4. The infusion apparatus of claim 3, wherein
   said rotary member is a disk mounted on a rotary shaft of said infusion pump,
   said reference mark means is a mark provided on a flat surface of the disk,
   said plurality of mark means are each an edge of slits provided radially at a peripheral portion of the disk, and
   said mark detection means is a photosensor.

5. The infusion apparatus of claim 3, wherein said live band determination means determines that said infusion pump is in the live band when the count value of said counter means is in a count value range corresponding to the live band.

6. The infusion apparatus of claim 4, wherein said live band determination means determines that said infusion pump is in the live band when the count value of said counter means is in a count value range corresponding to the live band.

7. An infusion apparatus comprising:
   fluid means, including an infusion pump, for delivering a fluid at a fluid delivery rate in an operation cycle, the operation cycle including a live band and a dead band;
   detection means for detecting the dead band; and
   correction means for correcting the fluid delivery rate of said fluid means based on the dead band detected by said detection means.

8. The infusion apparatus of claim 7, wherein the fluid delivery rate of said fluid means is less than a unit flow of said fluid means.

9. The infusion apparatus of claim 7, further comprising:
   a plurality of mark means provided at specified angles of rotation in a specified portion of a rotary member rotating together with the infusion pump, said specified portion corresponding to the live band of said fluid means;
   mark detection means for detecting one of said plurality of mark means to output a mark detection signal; and
   pump operation amount detection means for detecting an operation amount of said fluid means in the live band by counting a number of said plurality of mark means detected by said mark detection means based on the mark detection signal output from said mark detection means.

10. The infusion apparatus of claim 9, wherein said rotary member is a disk mounted on a rotary shaft of said infusion pump, said plurality of mark means are each an edge of a slit provided radially at a peripheral portion of the disk, and said mark detection means is a photosensor.

11. The infusion apparatus of claim 7, further comprising:

reference mark means provided on a rotary member rotating with said infusion pump, said reference mark means representing a reference position of said rotary member;

a plurality of mark means provided at specified angles of rotation on said rotary member;

mark detection means for detecting said reference mark means and one of said plurality of mark means to output a reference mark detection signal and a mark detection signal;

counter means, whose count value is cleared based on the reference mark detection signal and incremented based on the mark detection signal;

live band determination means for determining that said fluid means is in the live band based on the count value of said counter means; and pump operation amount detection means for detecting an operation amount of said fluid means by counting said plurality of mark means detected in the live band based on the mark detection signal output from said mark detection means in the live band.

12. The infusion apparatus of claim 11, wherein said rotary member is a disk mounted on a rotary shaft of said infusion pump, said reference mark means is a mark provided on a flat surface of the disk, said plurality of mark means are each an edge of slits provided radially at a peripheral portion of the disk, and said mark detection means is a photosensor.

13. The infusion apparatus of claim 11, wherein said live band determination means determines that said fluid means is in the live band when the count value of said counter means is in a count value range corresponding to the live band.

14. The infusion apparatus of claim 12, wherein said live band determination means determines that said fluid means is in the live band when the count value of said counter means is in a count value range corresponding to the live band.

15. An infusion method comprising the steps of:

delivering a fluid at a fluid delivery rate in an operation cycle of an infusion pump, the operation cycle including a live band and a dead band;

detecting the dead band; and correcting the fluid delivery rate of the infusion pump based on the detected dead band.

16. The infusion method of claim 15, wherein the fluid delivery rate of the infusion pump is less than a unit flow of the fluid means.

17. The infusion method of claim 15, wherein a plurality of marks are provided at specified angles of rotation in a specified portion of a rotary member rotating together with the infusion pump, said specified portion corresponding to the live band of the infusion pump;

said method further comprising the steps of:

detecting one of said plurality of marks to output a mark detection signal; and detecting an operation amount of the infusion pump in the live band by counting a number of the plurality of marks detected based on the mark detection signal.

18. The infusion method of claim 17, wherein the rotary member is a disk mounted on a rotary shaft of the infusion pump, the plurality of marks are each an edge of a slit provided radially at a peripheral portion of the disk, and the one of the plurality of marks is detected with a photosensor.

19. The infusion method of claim 15, wherein a reference mark is provided on a rotary member rotating with the infusion pump, the reference mark representing a reference position of the rotary member;

a plurality of marks are provided at specified angles of rotation on the rotary member;

said method further comprising the steps of:

detecting the reference mark and one of the plurality of marks to output a reference mark detection signal and a mark detection signal;

clearing a count value based on the reference mark detection signal and incrementing the count value based on the mark detection signal;

determining that the infusion pump is in the live band based on the count value; and detecting an operation amount of the infusion pump by counting the plurality of marks detected in the live band based on the mark detection signal output in the live band.

20. The infusion method of claim 19, wherein the rotary member is a disk mounted on a rotary shaft of the infusion pump, the reference mark is a mark provided on a flat surface of the disk, the plurality of marks are each an edge of slits provided radially at a peripheral portion of the disk, and the one of the plurality of marks is detected with a photosensor.

21. The infusion method of claim 19, wherein the infusion pump is in the live band when the count value is in a count value range corresponding to the live band.

22. The infusion method of claim 20, wherein the infusion pump is in the live band when the count value is in a count value range corresponding to the live band.

* * * * *